United States Patent
Le-Barillec et al.

(10) Patent No.: US 10,431,484 B2
(45) Date of Patent: Oct. 1, 2019

(54) METHOD AND STATION FOR MEASURING THE CONTAMINATION OF A TRANSPORT BOX FOR THE ATMOSPHERIC CONVEYANCE AND STORAGE OF SUBSTRATES

(71) Applicant: PFEIFFER VACUUM, Annecy (FR)

(72) Inventors: Olivier Le-Barillec, Pringy (FR); Julien Bounouar, Annecy (FR)

(73) Assignee: PFEIFFER VACUUM, Annecy (FR)

( * ) Notice: Subject to any disclaimer, the term of this patent is extended or adjusted under 35 U.S.C. 154(b) by 0 days.

(21) Appl. No.: 15/756,375

(22) PCT Filed: Aug. 29, 2016

(86) PCT No.: PCT/EP2016/070309
§ 371 (c)(1),
(2) Date: Feb. 28, 2018

(87) PCT Pub. No.: WO2017/037014
PCT Pub. Date: Mar. 9, 2017

(65) Prior Publication Data
US 2018/0247847 A1    Aug. 30, 2018

(30) Foreign Application Priority Data

Sep. 2, 2015 (FR) .................................. 15 58115

(51) Int. Cl.
| H01L 21/673 | (2006.01) |
| H01L 21/67 | (2006.01) |
| G01N 21/94 | (2006.01) |
| G01N 33/00 | (2006.01) |

(52) U.S. Cl.
CPC ....... H01L 21/67389 (2013.01); G01N 21/94 (2013.01); G01N 33/0036 (2013.01); H01L 21/67253 (2013.01)

(58) Field of Classification Search
CPC ................ G01N 21/94; G01N 33/0036; H01L 21/67253; H01L 21/67389
USPC .................................. 356/432–444, 335–343
See application file for complete search history.

(56) References Cited

FOREIGN PATENT DOCUMENTS

| JP | 10-199847 A | 7/1998 |
| KR | 10-1271181 B1 | 6/2013 |

OTHER PUBLICATIONS

International Search Report dated Dec. 1, 2016, in PCT/EP2016/070309 filed Aug. 29, 2016.

*Primary Examiner* — Tri T Ton
(74) *Attorney, Agent, or Firm* — Oblon, McClelland, Maier & Neustadt, L.L.P.

(57) ABSTRACT

A method for measuring contamination of a transport box for atmospheric conveyance and storage of substrates is provided, the method including: measuring a concentration of at least one gaseous species inside the transport box by a measurement device including at least one gas analyzer and a measurement line connecting the at least one gas analyzer to an interface, the interface placing the measurement line in communication with an internal atmosphere of the transport box; and supplying a gas flow containing water vapor to the measurement device. There is also provided a station for measuring contamination of a transport box for atmospheric conveyance and storage of substrates.

14 Claims, 1 Drawing Sheet

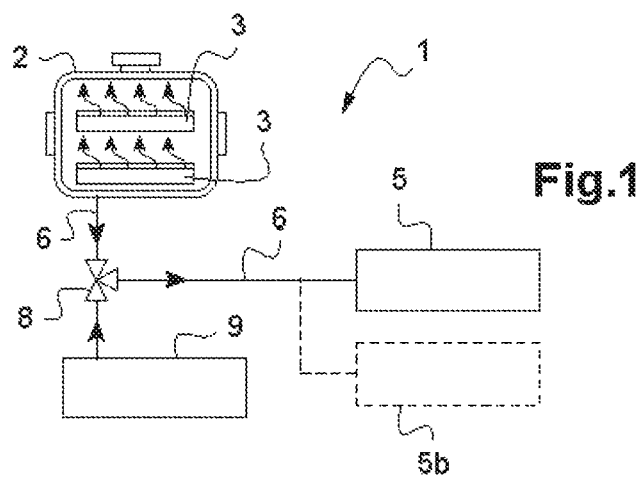
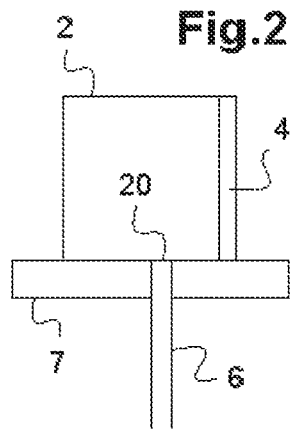
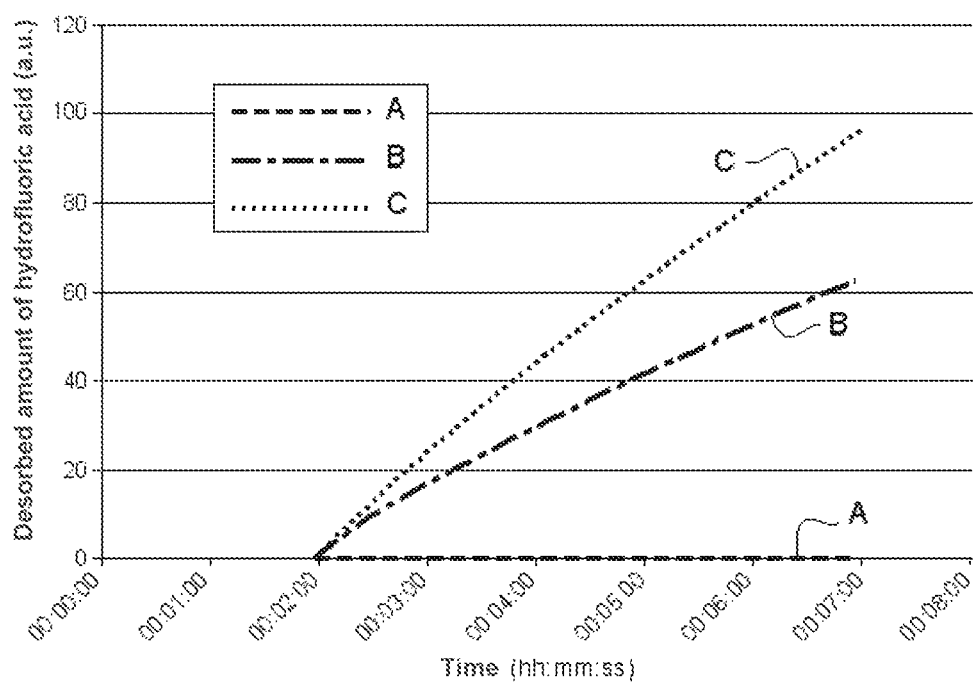

METHOD AND STATION FOR MEASURING THE CONTAMINATION OF A TRANSPORT BOX FOR THE ATMOSPHERIC CONVEYANCE AND STORAGE OF SUBSTRATES

TECHNICAL FIELD

The present invention relates to a method for measuring the contamination of a transport box for the atmospheric conveyance and storage of substrates, such as semiconductor wafers or photomasks. The invention also relates to a station for measuring the contamination of a transport box.

DESCRIPTION OF THE RELATED ART

In the semiconductor fabrication industry, the boxes for atmospheric transport and storage of substrates, such as semiconductor wafers or photomasks, define a confined volume at atmospheric pressure, isolated from the usage environment for the transport and storage of one or more substrates, from one piece of equipment to another or for storing the substrates between two fabrication steps.

A distinction is made in particular between standardized boxes for the transport and storage of wafers that are side-opening, of FOUP ("Front Opening Unified Pod") and FOSB ("Front Opening Shipping Box") type or that are bottom-opening, of SMIF Pod ("Standard Mechanical Interface Pod") type, "open cassette" boxes and standardized boxes for the transport and storage of photomasks, of RSP ("Reticle SMIF Pod") type.

These boxes made of plastic, such as polycarbonate, may be contaminated by fabrication process gases, such as HF, HCl, $NH_3$ and PGMEA gases, these gases being released in particular by the semiconductor wafers that have undergone prior fabrication operations.

The gases released may be adsorbed onto the internal surfaces of the boxes, then diffuse into the polymer, leading to the accumulation of pollutant molecules in the polymer. These pollutant molecules may subsequently desorb, then be adsorbed onto the substrates stored in these boxes, and optionally react chemically with the surface, which may create defects on the surfaces of the substrates.

Hydrofluoric acid in gaseous form in particular is a compound that particularly impacts the fabrication yield of electronic chips. Specifically, this molecule may generate defects on the semiconductor wafer. These defects, generally in the form of crystals, may be behind malfunctions of the chips.

One method used today for measuring the pollutant gaseous species potentially present in the transport boxes consists in carrying out a sampling by bubbling in deionized water. The sampling is analysed by ion chromatography. This operation is quite long, it lasts on average two hours, and can only be carried out when production is off-line.

Another known method is described in document EP 1 703 547. The internal atmosphere of transport boxes is monitored by efficient external analysis means placed in communication with the internal atmosphere of the transport box. Owing to this arrangement, it is possible to carry out an analysis in real time, during production, of traces of pollutant gases contained in the transport boxes.

This measurement of contamination of the substrate transport boxes should be carried out at high speed in order not to disrupt the production yield. However, when a contaminating species is measured in a large amount in the internal atmosphere of a transport box, the measurement line that places the box in communication with the analysis means may be significantly contaminated. It is then necessary to decontaminate the line prior to any new box monitoring in order to avoid distorting a subsequent measurement.

However, decontaminating the measurement line after a polluting gaseous species has been detected may be lengthy. This is because hydrofluoric acid especially adheres particularly to the walls due to the polar nature of the molecule. This phenomenon may therefore increase the waiting time between two consecutive measurements in order for the concentration of hydrofluoric acid to return to a low level for which the impact on the next measurement has become negligible. Also, during the measurement, the absorption of hydrofluoric acid on the walls may prevent its detection by the analysis means.

SUMMARY

One of the objectives of the present invention is to propose a method and a station that make it possible to reduce the waiting time between two measurements. Another objective of the present invention is to facilitate the measurement of the contaminating gaseous species present in the transport box.

For this purpose, one subject of the invention is a method for measuring the contamination of a transport box for the atmospheric conveyance and storage of substrates in which the concentration of at least one gaseous species inside the transport box is measured by a measurement device comprising at least one gas analyser and a measurement line connecting said at least one gas analyser to an interface, the interface placing the measurement line in communication with the internal atmosphere of at least one transport box, characterized in that a gas flow containing water vapour is supplied to the measurement device.

The inventors have indeed observed that the degree of humidity of the gas flow introduced into the measurement device influences the capacity of certain contaminating gaseous species, such as hydrofluoric acid, to desorb from the walls. Their experiments show that the introduction of a wet gas stream makes it possible to accelerate the desorption of the contaminating gaseous species.

According to one or more features of the measurement process, taken alone or in combination,
- at least one gaseous species, the concentration of which is measured, is hydrofluoric acid,
- the gas flow containing water vapour has a degree of humidity of greater than 40%, for instance greater than 95%,
- the gas stream containing water vapour is moist air,
- a gas flow containing water vapour is supplied to the measurement device while a contamination measurement is carried out,
- a gas flow containing water vapour is supplied to the measurement device after having carried out a contamination measurement and isolated the interface,
- a gas flow containing water vapour is supplied to the measurement device after having carried out a contamination measurement for which the concentration of the gaseous species has exceeded a predetermined threshold,
- a gas flow containing water vapour is supplied to the measurement device after each gaseous species measurement,
- a gas flow having a first degree of humidity is supplied if the concentration of the gaseous species is lower than a predetermined threshold and a gas flow having a second degree of humidity greater than the first degree of humidity is supplied if the concentration of the gaseous species exceeds the predetermined threshold.

Another subject of the invention is a station for measuring the contamination of a transport box for the atmospheric conveyance and storage of substrates, comprising:

a measurement device comprising at least one gas analyser and a measurement line connected to said at least one gas analyser, and an interface for placing the measurement line in communication with the internal atmosphere of at least one transport box so as to carry out an analysis of at least one gaseous species contained in the internal atmosphere of the transport box by said at least one gas analyser, characterized in that it comprises a humidity generator configured in order to supply a gas stream containing water vapour to the measurement device.

According to one or more features of the measurement station, taken alone or in combination, the humidity generator is coupled to the measurement line connecting said at least one gas analyser to the interface, the measurement station comprising at least one valve arranged on the measurement line, the valve being configured in order to place the interface in communication with said at least one gas analyser or to place said at least one gas analyser in communication with the humidity generator, said at least one gas analyser comprises a sampling pump, said at least one gas analyser comprises an optical sensor that operates by absorption spectroscopy.

BRIEF DESCRIPTION OF THE DRAWINGS

Other features and advantages of the invention will emerge from the following description, given by way of example, with no limiting nature, with regard to the appended drawings in which:

FIG. 1 represents a schematic view of elements of a station for measuring the contamination of a transport box, FIG. 2 represents an example of an interface of the measurement station from FIG. 1, and FIG. 3 is a graph representing the amount of hydrofluoric acid desorbed from the walls of the measurement device as a function of the time and of the degree of humidity of the gas flow introduced into the measurement device.

In these figures, identical elements bear the same reference numbers.

The following embodiments are examples. Although the description refers to one or more embodiments this does not necessarily mean that each reference relates to the same embodiment, or that the features apply only to one embodiment. Simple features of various embodiments may also be combined in order to provide other embodiments.

DETAILED DESCRIPTION

FIG. 1 represents a station 1 for measuring the contamination of a transport box 2 for the atmospheric conveyance and storage of substrates 3.

The transport box 2 may in particular be a standardized transport box of FOUP, FOSB, SWF Pod, RSP or "Open Cassette" type.

Use is made, for example, of standardized front-opening FOUP-type transport boxes 2, as illustrated in FIG. 1.

The transport box 2 is made of plastic, such as for example polycarbonate.

The transport box 2 comprises walls confining an internal volume intended for storing substrates 3, such as semiconductor wafers or photomasks.

As represented schematically in FIG. 2, such FOUP-type transport boxes 2 comprise a front-opening door 4 sized for the introduction and extraction of the substrates 3, and generally comprise one or more lower orifices 20 provided with a filter that protects the substrates 3 from the particulate contamination that may originate from the environment outside the transport box 2.

The transport box 2 delimits a confined volume. Nevertheless, the ambient air may pass through the leaks of the door seal and through the orifices 20, by favouring however leakage through the filters of the orifices 20. The orifices 20 that comprise filters enable the ambient air to enter and leave, in order to balance the pressures in particular during the closing and opening of the door 4.

The measurement station 1 comprises a measurement device and an interface 7.

The measurement device comprises at least one gas analyser 5, 5b and a measurement line 6 connected to said at least one gas analyser 5, 5b.

The measurement line 6 is for example made of perfluoroalkoxy (also referred to as PFA) or of polytetrafluoroethylene (also referred to as PTFE), in order to limit the adhesion of the polluting gaseous species to the walls.

The interface 7 makes it possible to place the measurement line 6 in communication with the internal atmosphere of at least one transport box 2 so as to carry out an analysis of at least one gaseous species potentially present in the internal atmosphere of the transport box 2, using one or more gas analysers 5, 5b.

The transport box 2 is for example positioned on the interface 7 by means of standardized positioning pins. The interface 7 additionally comprises means for retaining the transport box 2, such as pivoting locking pins.

The interface 7 provides the connection between the transport box 2, via its orifice 20, and the measurement line 6 that conveys the gases to the inlet of at least one gas analyser 5, 5b.

If the transport box has no orifice 20 in its lower wall, the interface 7 then comprises means for opening the door of the transport box, and collection means that ensure a sufficient isolation with respect to the atmosphere of the cleanroom. Provision is then made for the measurement to be taken when the door of the transport box is slightly open.

The measurement station 1 also comprises a humidity generator 9.

The humidity generator 9 is configured in order to supply a gas stream containing water vapour with a relative humidity of greater than 0% and less than 100%, which is not condensed, to the measurement device, that is to say to the measurement line 6 and/or to at least one gas analyser 5, 5b.

The humidity generator 9 is for example coupled to the measurement line 6 connecting at least one gas analyser 5, 5b to the interface 7.

The measurement station 1 may comprise a three-way valve 8 arranged on the measurement line 6. The three-way valve 8 is, on the one hand, configured in order to place the interface 7 in communication with at least one gas analyser 5, 5b, the humidity generator 9 then being isolated from the interface 7 and from the at least one gas analyser 5, 5b. The three-way valve 8 is, on the other hand, configured in order to place said at least one gas analyser 5, 5b in communication with the humidity generator 9, the interface 7 then being isolated from the humidity generator 9 and from the at least one gas analyser 5, 5b. Alternatively, it is possible to provide, for example, a separate valve in each branch of the measurement line 6 in order to carry out the same role.

According to one exemplary embodiment, the gas analyser 5, 5b comprises a small sampling pump, the sampling flow rate of which is less than 5 SLM (Standard Liters Per Minute), for instance of the order of 1.2 SLM.

Thus, according to a first example of the implementation of the measurement method, the gas flow containing water vapour may be conveyed, by pump sampling, from the humidity generator 9 to the gas analyser 5, 5b, the interface 7 then being isolated from the humidity generator 9 and from the gas analyser 5, 5b.

Similarly, the gaseous species to be measured may be conveyed, by pump sampling, from the transport box 2 to the gas analyser 5, 5b, the humidity generator 9 then being isolated from the interface 7 and from the gas analyser 5, 5b.

The gas analyser 5, 5b makes it possible to measure the concentration of at least one gaseous species in real time, that is to say with a measurement time of less than a few seconds, or even a few minutes, for low concentrations of the order of ppm or ppb.

According to one exemplary embodiment, the gas analyser 5, 5b comprises an optical sensor that operates on the principle of absorption spectroscopy for absorption of the wavelength of a laser by a gaseous species to be measured, such as for example the CRDS (Cavity Ring-Down Spectroscopy) principle. For this, the gas analyser 5, 5b comprises an optical cavity in contact with the gaseous species to be measured and a laser configured in order to illuminate the optical cavity with a predefined wavelength.

When a gaseous species passes through the optical cavity, this species absorbs the light which decreases in correlation. The time it takes for the initial intensity of the light to decay is measured, and this time may be used to calculate the concentration of the absorbing substance in the gas mixture present in the optical cavity.

In use, the three-way valve 8 is firstly oriented so as to place the gases originating from a transport box 2 positioned on the interface 7 in communication with at least one gas analyser 5, 5b. The humidity generator 9 is then isolated from the interface 7 and from the at least one gas analyser 5, 5b.

The concentration of at least one gaseous species, potentially present inside the transport box 2 and potentially polluting, is measured by at least one gas analyser 5, 5b.

The gaseous species measured is for example an acid, such as hydrofluoric acid HF or hydrochloric acid HCl or a solvent, such as PGMEA (propylene glycol methyl ether acetate).

According to another example, the gaseous species is ammonia $NH_3$.

In case where the measurement device comprises several gas analysers 5, 5b, provision may be made for each gas analyser 5, 5b to be suitable for the measurement of a distinct gaseous species or a group of distinct gaseous species.

Thus, for example, a first gas analyser 5 is suitable for measuring hydrofluoric acid HF, a second gas analyser 5b is suitable for measuring hydrochloric acid HCl and a third gas analyser (not represented) is suitable for measuring ammonia $NH_3$.

In the example illustrated in FIG. 3, the gaseous species measured is hydrofluoric acid HF.

The measurement is carried out over a time for example of the order of two minutes. During this time, if hydrofluoric acid HF is present in the internal atmosphere of the transport box 2, a proportion of the hydrofluoric acid HF will pass into the volume of the analysis cell, whereas the remaining proportion will be adsorbed on the internal walls of the measurement line 6 and of the gas analyser 5.

After the measurement, the gas analyser 5 is placed in communication with the humidity generator 9 and a gas flow containing water vapour is supplied to the measurement device. The interface 7 is then isolated from the humidity generator 9 and from the gas analyser 5.

The gas flow containing water vapour is introduced into the measurement device, that is to say into the portion of the measurement line 6 connecting the humidity generator 9 to the gas analyser 5. The gas flow containing water vapour thus flows from the humidity generator 9 to the gas analyser 5 through the measurement line 6. The gas flow containing water vapour may also be introduced directly into the gas analyser 5 of the measurement device.

The gas flow containing water vapour is a gas mixture having a degree of humidity of greater than 0% at ambient temperature (20° C.), for example greater than 20% humidity.

Provision is made, for example, for the gas flow to have a degree of humidity of greater than 40%, for instance greater than 95%. It is thus greater than the degree of humidity of the cleanroom which is generally close to 40%.

The gas flow containing water vapour is for example moist air formed for example from a mixture of dry air of CDA (Compressed Dry Air) type and water vapour so as to better control the degree of humidity. According to another example, the gas flow containing water vapour is a mixture of nitrogen and water vapour.

The introduction of the gas flow containing water vapour into the measurement device may be carried out when a measurement of the concentration of hydrofluoric acid HF is greater than a predetermined threshold.

Alternatively, the introduction of the gas flow containing water vapour into the measurement device is carried out after each measurement of the concentration of hydrofluoric acid HF. Provision may additionally be made to supply a gas flow having a first degree of humidity if the concentration of hydrofluoric acid HF is lower than a predetermined threshold and to supply a gas flow having a second degree of humidity greater than the first degree of humidity if the concentration of hydrofluoric acid HF exceeds the predetermined threshold.

FIG. 3 represents the amount of hydrofluoric acid HF desorbed as a function of the time in a measurement device as a function of various degrees of humidity of the air introduced.

The measurement line 6 and the gas analyser 5 are contaminated beforehand so as to have the same amount of absorbed hydrofluoric acid HF. Air flows containing various degrees of humidity originating from the humidity generator 9 are then introduced into the measurement line 6, and correspond to the various curves described below.

Curve A corresponds to the amount of hydrofluoric acid HF desorbed by the measurement line 6 and the gas analyser 5 following the introduction of dry air, curve B corresponds to the amount of hydrofluoric acid HF desorbed following the introduction of air having a degree of humidity of the order of 32% and curve C corresponds to the amount of hydrofluoric acid HF desorbed following the introduction of air having 63% humidity.

It is observed from this graph that the higher the degree of humidity of the air, the more the amount of hydrofluoric acid HF desorbed increases (curves B and C).

It is also observed that the amount of hydrofluoric acid HF desorbed is virtually zero for an injection of dry air into the measurement device (curve A).

Thus, the degree of humidity of the gas flow introduced in order to decontaminate the measurement device influences the capacity of hydrofluoric acid HF to desorb from the walls.

Following the introduction of a dry gas flow (curve A), hydrofluoric acid HF remains absorbed on the walls. On the other hand, the introduction of humidity into the measurement line 6 and also into the gas analyser 5 makes it possible to accelerate the desorption of hydrofluoric acid HF from the walls.

It is therefore possible to accelerate the decontamination of the measurement device between two successive measurements by introducing a moist gas flow into the measurement device and therefore to reduce the waiting time between two measurements.

According to a second example of implementation of the measurement method, a gas flow containing water vapour is supplied to the measurement device while a contamination measurement is carried out.

For this, the humidity generator 9 is placed in communication both with the interface 7 and the at least one gas analyser 5, 5b. The gas flow containing water vapour is introduced into the measurement line 6 connecting the at least one gas analyser 5, 5b to the interface 7 while the at least one gas analyser 5, 5b carries out a contamination measurement.

Provision is also made for the gas flow containing water vapour to be less than the flow sampled by the pump of the at least one gas analyser 5, 5b in order to prevent the gas flow containing water vapour from being able to "rise back up" into the transport box 2.

The concentration of the gaseous species diluted by the gas flow containing water vapour can be found again by applying a proportional corrective factor. For example, the measurement result is multiplied by two if half of the gas flow measured originates from the transport box 2 and the other half originates from the humidity generator 9.

This measurement method is particularly advantageous for the measurement of the contamination of transport boxes 2 purged under a dry atmosphere. This is because the dry purge gas of the transport box 2 that is sampled by the gas analyser 5, 5b, favours the absorption of hydrofluoric acid on the walls. By providing moist air to the measurement device during the measurement, the transport of hydrofluoric acid to the gas analyser 5, 5b is facilitated which makes it possible to better see the gaseous species present in the transport box 2.

The invention claimed is:

1. A method for measuring contamination of a transport box for atmospheric conveyance and storage of substrates, the method comprising:
    measuring a concentration of at least one gaseous species inside the transport box by a measurement device comprising at least one gas analyzer and a measurement line connecting the at least one gas analyzer to an interface, the interface placing the measurement line in communication with an internal atmosphere of the transport box; and
    supplying a gas flow containing water vapor to the measurement device.

2. The method according to claim 1, wherein the at least one gaseous species is hydrofluoric acid (I-IF).

3. The method according to claim 1, wherein the gas flow containing the water vapor has a degree of humidity of greater than 40%.

4. The method according to claim 1, wherein the gas flow containing the water vapor has a degree of humidity of greater than 95%.

5. The method according to claim 1, wherein the gas flow containing the water vapor is moist air.

6. The method according to claim 1, wherein the gas flow containing the water vapor is supplied to the measurement device while a contamination measurement is carried out.

7. The method according to claim 1, wherein the gas flow containing the water vapor is supplied to the measurement device after having carried out a contamination measurement and isolating the interface.

8. The method according to claim 1, wherein the gas flow containing the water vapor is supplied to the measurement device after having carried out a contamination measurement for which the measured concentration of the at least one gaseous species has exceeded a predetermined threshold.

9. The method according to claim 7, wherein the gas flow containing the water vapor is supplied to the measurement device after each gaseous species measurement.

10. The method according to claim 1, wherein a gas flow having a first degree of humidity is supplied if the measured concentration of the at least one gaseous species is lower than a predetermined threshold, and a gas flow having a second degree of humidity greater than the first degree of humidity is supplied if the measured concentration of the at least one gaseous species exceeds the predetermined threshold.

11. A station for measuring contamination of a transport box for atmospheric conveyance and storage of substrates, the station comprising:
    a measurement device comprising at least one gas analyzer and a measurement line connected to the at least one gas analyzer;
    an interface for placing the measurement line in communication with an internal atmosphere of the transport box so as to carry out an analysis of at least one gaseous species contained in the internal atmosphere of the transport box by the at least one gas analyzer; and
    a humidity generator configured to supply a gas stream containing water vapor to the measurement device.

12. The station according to the claim 11, wherein the humidity generator is coupled to the measurement line connecting the at least one gas analyzer to the interface, the measurement station comprising at least one valve arranged on the measurement line, the at least one valve being configured to place the interface in communication with the at least one gas analyzer or to place the at least one gas analyzer in communication with the humidity generator.

13. The station according to claim 11, wherein the at least one gas analyzer comprises a sampling pump.

14. The station according to claim 11, wherein the at least one gas analyzer comprises an optical sensor that operates by absorption spectroscopy.

* * * * *